United States Patent
Baroni et al.

(12)

(10) Patent No.: US 7,211,578 B2
(45) Date of Patent: May 1, 2007

(54) NITROGENOUS TETRAHYDROPYRIDYL-ALKYL-HETEROCYCLES WITH TNF ACTIVITY

(75) Inventors: Marco Baroni, Vanzago-Milano (IT); Bernard Bourrie, Saint-Gely-du Fesc (FR); Pierre Casellas, Montpellier (FR); Letizia Puleo, Milan (IT)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 10/495,890

(22) PCT Filed: Nov. 18, 2002

(86) PCT No.: PCT/FR02/03929

§ 371 (c)(1),
(2), (4) Date: May 18, 2004

(87) PCT Pub. No.: WO03/044010

PCT Pub. Date: May 30, 2003

(65) Prior Publication Data

US 2005/0004132 A1    Jan. 6, 2005

(30) Foreign Application Priority Data

Nov. 19, 2001 (FR) .................................. 01 14897

(51) Int. Cl.
  *C07D 401/10*  (2006.01)
  *A61K 31/4523*  (2006.01)
  *A61K 31/4545*  (2006.01)

(52) U.S. Cl. ................... 514/252.01; 514/253.01; 514/256; 514/332; 514/333; 544/238; 544/333; 544/405; 546/255; 546/256

(58) Field of Classification Search ................ 514/332, 514/333, 252.03, 253.01, 256; 546/255, 546/256; 544/238, 333, 405
See application file for complete search history.

(56) References Cited

U.S. PATENT DOCUMENTS 6,034,090 A    3/2000 Baroni et al.
6,509,351 B1   1/2003 Baroni et al.

FOREIGN PATENT DOCUMENTS

| JP | 48085572 | * 11/1973 |
| WO | WO 98/25903 | 6/1998 |
| WO | WO 01/29026 | 4/2001 |

OTHER PUBLICATIONS

Chemical Abstract, Nakanishi et al, 80:37011 (Abstract of JP 48085572), 1974.*

* cited by examiner

*Primary Examiner*—Zinna N. Davis
(74) *Attorney, Agent, or Firm*—Julie Anne Knight; Raymond S. Parker; Robert J. Kajubi

(57) ABSTRACT

This invention relates to nitrogenous (tetrahydropyridyl) (alkyl)heterocycles, to pharmaceutical compositions comprising them, to processes for preparing them and to the method of use thereof in the treatment of pain and diseases related to immune and inflammatory disorders.

47 Claims, No Drawings

NITROGENOUS TETRAHYDROPYRIDYL-ALKYL-HETEROCYCLES WITH TNF ACTIVITY

The present invention relates to novel nitrogenous (tetrahydropyridyl)(alkyl)heterocycles, in particular nitrogenous monocyclic heterocycles, to the pharmaceutical compositions comprising them and to a process for their preparation.

WO 98/25903 discloses 1-phenylalkyl-1,2,3,6-tetrahydropyridines for the treatment of Alzheimer's disease.

WO 01/29026 discloses phenyl- and pyridyltetrahydropyridines having an inhibitory activity with regard to TNF-α (Tumor Necrosis Factor).

Bourrié et al. (Proc. Natl. Acad. Sci., 1999, 96(22), 12855–12859) have described the activity of a compound known as SR 57746 (1-(2-(naphth-2-yl)ethyl)-4-(3-trifluoromethyl)-1,2,3,6-tetrahydropyridine) in an experimental autoimmune encephalomyelitis (EAE) model and in the modulation of TNF-α.

TNF-α is a cytokine which has recently aroused interest as mediator of immunity, inflammation, cell proliferation, fibrosis, and the like. This mediator is extensively present in inflamed synovial tissue and exerts an important role in the pathogenesis of autoimmunity (Annu. Rep. Med. Chem., 1997, 32, 241–250).

It has now been found that some tetrahydropyridines substituted by nitrogenous monocyclic heterocyclic derivatives have a powerful activity with regard to modulating TNF-α.

Thus, the present invention relates, according to one of its aspects, to (tetrahydropyridyl)(alkyl)benzodiazines of formula (I):

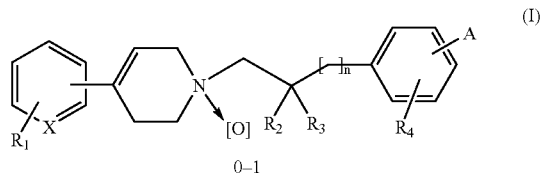

in which
X represents N or CH;
$R_1$ represents a hydrogen or halogen atom or a $CF_3$ group;
$R_2$ and $R_3$ independently represent a hydrogen atom or a $(C_1-C_4)$alkyl group;
$R_4$ represents a hydrogen atom or a $(C_1-C_4)$alkyl group;
n is 0 or 1;
A represents a nitrogenous heterocycle of formula (a)–(d):

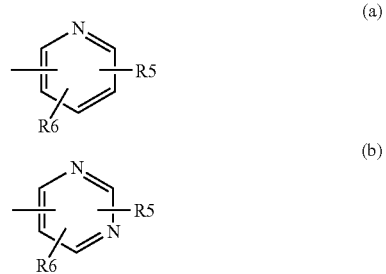

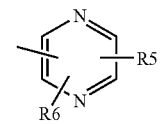

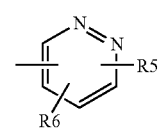

where $R_5$ and $R_6$ each independently represent a hydrogen atom or a $(C_1-C_4)$alkyl or $(C_1-C_4)$alkoxy group;
and their N-oxides and their salts or solvates.

In the present description, the term "$(C_1-C_4)$alkyl" denotes a monovalent radical of a saturated, straight- or branched-chain, $C_1-C_4$ hydrocarbon and the term "$(C_1-C_4)$alkoxy" denotes a monovalent radical of a saturated, straight- or branched-chain, $C_1-C_4$ hydrocarbon bonded via an oxygen atom.

In the present description, the term "halogen" denotes an atom chosen from chlorine, bromine, iodine and fluorine.

Preferred compounds of formula (I) are those where n is zero.

Other preferred compounds are those where $R_2$ and $R_3$ are hydrogen.

Other preferred compounds are those where $R_1$ is a $CF_3$ group.

Other preferred compounds are those where X is CH and $R_1$ is in the 3-position of the benzene.

Other preferred compounds are those where X is CH and $R_1$ is a $CF_3$ group.

Other preferred compounds are those where X is N and the pyridine thus formed is substituted in the 2,6-positions.

Other preferred compounds are those where the phenyl ring is substituted by the nitrogenous heterocycle A in the 3-position.

The nitrogenous heterocycles of formula (a)–(d) respectively represent a pyridine, a pyrimidine, a pyrazine or a pyridazine. These heterocycles can, according to the present invention, be attached to the remainder of the molecule of formula (I) via any one of the carbon atoms of the available positions.

According to the present invention, the compounds of formula (I) can exist as N-oxide derivatives. As indicated in the above formula, the compounds of formula (I) can in particular carry the N-oxide group on the tetrahyropyridine; alternatively, N-oxide groups may be present on the nitrogens of the groups (a)–(d) and, optionally, all the nitrogens of the compounds of formula (I) can be simultaneously oxidized.

The salts of the compounds of formula (I) according to the present invention comprise both addition salts with pharmaceutically acceptable inorganic or organic acids, such as the hydrochloride, hydrobromide, sulfate, hydrogensulfate, dihydrogen-phosphate, citrate, maleate, tartrate, fumarate, gluconate, methanesulfonate, 2-naphthalenesulfonate, and the like, and addition salts which make possible suitable separation or crystallization of the compounds of formula (I), such as the picrate or oxalate, or addition salts with optically active acids, for example camphorsulfonic acids and mandelic or substituted mandelic acids.

The optically pure stereoisomers and the mixtures of isomers of the compounds of formula (I) due to the asymmetric carbon, when one of $R_2$ and $R_3$ are different from one another, in any proportion, form part of the present invention.

The compounds of formula (I) can be prepared by a condensation reaction from a compound of formula (II):

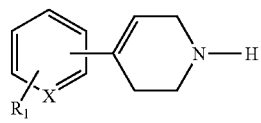
(II)

in which X and $R_1$ are as defined above, with a compound of formula (III):

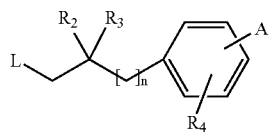
(III)

in which $R_2$, $R_3$, $R_4$, n and A are as defined above and L is a leaving group, isolation of the compound of formula (I) and optional conversion to one of its salts or solvates or to its N-oxide derivatives.

The condensation reaction is normally carried out by mixing the starting compounds (II) and (III) in an inert organic solvent according to conventional methods.

The term "inert organic solvent" is understood to mean a solvent which does interfere with the reaction. Such solvents are, for example, alcohols, such as methanol, ethanol, propan-2-ol or butanol.

It is possible, as leaving group L, for example, to use a halogen, such as a chlorine or bromine atom, or else a methylsulfonyloxy group ($CH_3$—$SO_2$—O—).

The reaction is carried out at a temperature of between $-10°$ C. and the reflux temperature of the reaction mixture, the reflux temperature being preferred.

The reaction can be suitably carried out in the presence of a proton acceptor, for example of an alkaline carbonate or of a tertiary amine, such as triethylamine.

The reaction is generally brought to a conclusion after a few hours; usually from 1 to 6 hours suffice to bring the condensation to completion.

The required compound is isolated according to conventional techniques in the free base form or in the form of one of its salts. The free base can be converted to one of its salts by simple salification in an organic solvent, such as an alcohol, preferably ethanol or isopropanol, an ether, such as 1,2-dimethoxyethane, ethyl acetate, acetone or a hydrocarbon, such as hexane.

The compound of formula (I) obtained is isolated according to conventional techniques and is optionally converted to one of its salts or solvates or to its N-oxide derivatives.

The starting compounds of formula (II) are known or else they can be prepared analogously to the known compounds.

The starting compounds of formula (III) are novel and constitute a further subject matter of the present invention. These compounds can be prepared from the corresponding acids or esters by reduction of the carboxyl group to an alcohol group and substitution of the OH by the desired L group according to conventional methods. Alternatively, these compounds are prepared by Stille or Suzuki coupling of the two suitably substituted phenyl and heterocycle rings; according to these couplings, a suitable halophenyl is reacted with respectively trialkylstannane or diborane derivatives of a heterocycle ring or, conversely, an appropriate haloheterocycle is reacted with respectively trialkylstannane or diborane derivatives of the phenyl ring. After the coupling, the rings are optionally functionalized by conversion of the groups present, according to well known methods. Examples of the preparation of nitrogenous (trialkylstannane)heterocyclic compounds are reported in Bioorganic and Medicinal Chemistry, 9/2001, 2683–2691. Other examples of the above reactions are recorded in the experimental part.

Alternatively, the compounds of formula (I) can also be prepared by a process which plans:

(a) to react the compound of formula (VI):

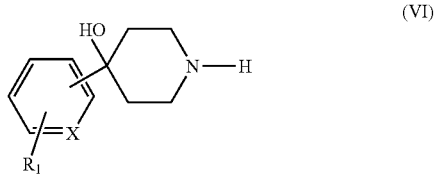
(VI)

in which X and $R_1$ are defined as above, with a functional derivative of the acid of formula (VII)

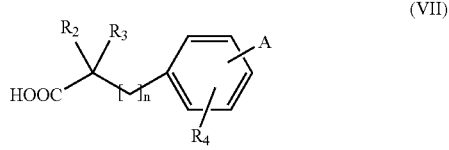
(VII)

in which $R_2$, $R_3$, $R_4$, n and A are as defined above, (b) to reduce the carbonyl group of the compound of formula (VIII) thus obtained:

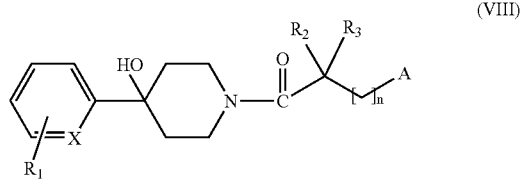
(VIII)

(c) to dehydrate the intermediate piperidinol of formula (IX) thus obtained:

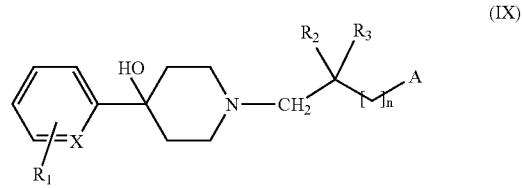
(IX)

(d) to isolate the compound of formula (I) thus obtained and, optionally, to convert it to one of its salts or solvates or to its N-oxide derivatives.

The reaction of stage (a) can be suitably carried out in an organic solvent at a temperature of between −10° C. and the reflux temperature of the reaction mixture.

It may be preferable to carry out the reaction under cold conditions when it is exothermic, as in the case where the chloride is used as functional derivative of the acid of formula (VII).

The acids of formula (VII) above are novel and represent a further subject matter of the present invention. These compounds can be prepared from the products obtained by the Stille or Suzuki couplings mentioned above, in particular by conversion of the substituents present on the phenyl to the desired acid groups.

Use may be made, as appropriate functional derivative of the acid of formula (VII), of the free acid, which is optionally activated (for example with BOP=tri(dimethylamino)benzotriazol-1-yloxyphosphonium hexafluorophosphate), an anhydride, a mixed anhydride, an active ester or an acid halide, preferably the bromide. Among the active esters, the p-nitrophenyl ester is particularly preferred but the methoxyphenyl, trityl, benzhydryl and similar esters are also suitable.

Use is preferably made, as reaction solvent, of a halogenated solvent, such as methylene chloride, dichloroethane, 1,1,1-trichloroethane, chloroform and the like, but also other organic solvents compatible with the reactants employed, for example dioxane, tetrahydrofuran or a hydrocarbon, such as hexane, can likewise be employed.

The reaction can be suitably carried out in the presence of a proton acceptor, for example of an alkaline carbonate or of a tertiary amine, such as triethylamine.

The reduction of stage (b) can be suitably carried out with appropriate reducing agents, such as borane complexes, for example borane-dimethyl sulfide ($[CH_3]_2S$—$BH_3$), aluminum hydrides or a complex hydride of lithium and of aluminum, in an inert organic solvent at a temperature of between 0° C. and the reflux temperature of the reaction mixture, according to conventional techniques.

The term "inert organic solvent" is understood to mean a solvent which does not interfere with the reaction. Such solvents are, for example, ethers, such as diethyl ether, tetrahydrofuran (THF), dioxane or 1,2-dimethoxyethane.

Alternatively, the compounds of formula (I) can also be prepared by a condensation/reduction reaction, starting from a compound of formula (II):

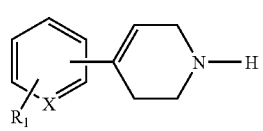

(II)

in which X and $R_1$ are as defined above, with an aldehyde of formula (X):

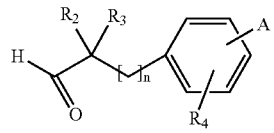

(X)

in which $R_2$, $R_3$, $R_4$, n and A are as defined above, isolation of the compound of formula (I) and optional conversion to one of its salts or solvates or to its N-oxide derivatives.

The condensation/reduction reaction is carried out by mixing the starting compounds (II) and (X) in an organic solvent, such as an alcohol, such as, for example, methanol, in an acidic medium, in the presence of a reducing agent, such as sodium cyanoborohydride, according to conventional methods.

The compounds of formula (I) carrying an N-oxide group on the nitrogen atoms of the groups (a)–(d) can be prepared from the N-oxide derivatives of the compounds of formula (III) or (X).

The compounds of formula (I) carrying an N-oxide group on the nitrogen atom of the tetrahydropyridine or of the pyridine bonded to the tetrahydropyridine when X is N can be prepared by oxidation of the corresponding compounds of formula (I). In this case, the compound of formula (I), such as obtained, for example, by the above synthesis, is subjected to an oxidation reaction according to conventional methods, for example to a reaction with m-chloroperbenzoic acid, in a suitable solvent, and is isolated according to conventional techniques well known to a person skilled in the art.

The compounds of the invention have properties which are advantageous with respect to the inhibition of TNF-α.

These properties were demonstrated using a test aimed at measuring the effect of molecules on TNF-α synthesis induced in Balb/c mice by lipopolysaccharide (LPS) of *Escherichia coli* (055:B5, Sigma, St Louis, Mo.).

The products to be tested are administered orally to groups of 5 female Balb/c mice (Charles River, France) aged from 7 to 8 weeks. One hour later, the LPS is administered intravenously (10 μg/mouse). A blood sample is taken from each animal 1.5 hours after administration of the LPS. The samples are centrifuged and the plasma is recovered and frozen at −80° C. The TNF-α is measured using commercial kits (R and D, Abingdon, UK).

In this test, compounds representative of the invention proved to be very active, inhibiting TNF-α synthesis even at very low doses.

Due to this activity and to their low toxicity, the compounds of formula (I) and its salts or solvates can indeed be used in the treatment of diseases related to immune and inflammatory disorders or as analgesics. In particular, the compounds of formula (I) can be used to treat atherosclerosis, autoimmune diseases, diseases which lead to the demyelinization of neurones (such as multiple sclerosis), asthma, rheumatoid arthritis, fibrotic diseases, idiopathic pulmonary fibrosis, cystic fibrosis, glumerulonephritis, rheumatoid spondylitis, osteoarthritis, gout, bone and cartilage resorption, osteoporosis, Paget's disease, multiple myeloma, uveoretinitis, septic shock, septicemia, endotoxic shock, graft-versus-host reaction, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, lupus erythematosus disseminatus, hemodynamic shock; ischemic pathological conditions (myocardial infarction, myocardial ischemia, coronary vasospasm, angina pectoris, cardiac insufficiency, heart attack), postischemic reperfusion injuries, malaria, mycobacterial infections, meningitis, leprosy, viral infections (HIV, cytomegalovirus, herpes virus), AIDS-related opportunistic infections, tuberculosis, psoriasis, atopic and contact dermatosis, diabetes, cachexia, cancer and radiation-mediated damage.

The compounds of formula (I) and their pharmaceutically acceptable salts and solvates are preferably administered orally.

In the oral pharmaceutical compositions of the present invention, the active principle can be administered in unit administration forms, as a mixture with conventional pharmaceutical carriers, to animals and human beings for the treatment of the abovementioned conditions. The appropriate unit administration forms comprise, for example, tablets, optionally scored, gelatin capsules, powders, granules and solutions or suspensions to be taken orally.

When a solid composition is prepared in the form of tablets, the main active ingredient is mixed with a pharmaceutical vehicle, such as gelatin, starch, lactose, magnesium stearate, talc, gum arabic or the like. The tablets can be coated with sucrose or other appropriate materials or can be treated so that they have a prolonged or delayed activity and so that they continuously release a predetermined amount of active principle.

A preparation in the form of gelatin capsules is obtained by mixing the active ingredient with a diluent and by pouring the mixture obtained into soft or hard gelatin capsules.

A preparation in the syrup or elixir form can comprise the active ingredient in conjunction with a sweetener, preferably a calorie-free sweetener, methylparaben and propylparaben as antiseptics, and an appropriate colorant and flavoring.

The water-dispersible powders or granules can comprise the active ingredient as a mixture with dispersing agents, wetting agents or suspending agents, such as polyvinylpyrrolidone, and with sweeteners or flavor enhancers.

The active principle can also be formulated in the form of microcapsules, optionally with one or more carriers or additives.

In the pharmaceutical compositions according to the present invention, the active principle can also be in the form of an inclusion complex in cyclodextrins, their ethers or their esters.

The amount of active principle to be administered depends, as always, on the degree of progression of the disease and also on the age and weight of the patient. Nevertheless, the unit doses generally comprise from 0.001 to 100 mg, better still from 0.01 to 50 mg, preferably from 0.1 to 20 mg, of active principle, advantageously from 0.5 to 10 mg.

According to another of its aspects, the present invention relates to a combination comprising a compound of formula (I) or one of its pharmaceutically acceptable salts or solvates and at least one compound chosen from immunosuppressants, such as interferon beta-1b; adrenocorticotropic hormone; glucocorticoids, such as prednisone or methylprednisolone; or interleukin-1 inhibitors.

More particularly, the invention relates to a combination comprising a compound of formula (I) or one of its pharmaceutically acceptable salts or solvates and at least one compound chosen from roquinimex (1,2-dihydro-4-hydroxy-N,1-dimethyl-2-oxo-3-quinoline-carboxanilide), myloran (product from Autoimmune comprising bovine myelin), antegren (monoclonal human antibody from Elan/Athena Neurosciences) or recombinant interferon beta-1b.

Other possible combinations are those composed of a compound of formula (I) or one of its pharmaceutically acceptable salts or solvates and a potassium-channel blocker, such as, for example, fampridine (4-aminopyridine).

According to another of its aspects, the invention relates to a method for the treatment of diseases related to immune and inflammatory disorders and in the treatment of pain, in particular atherosclerosis, autoimmune diseases, diseases which lead to the demyelinization of neurones (such as multiple sclerosis), asthma, rheumatoid arthritis, fibrotic diseases, idiopathic pulmonary fibrosis, cystic fibrosis, glumerulonephritis, rheumatoid spondylitis, osteoarthritis, gout, bone and cartilage resorption, osteoporosis, Paget's disease, multiple myeloma, uveoretinitis, septic shock, septicemia, endotoxic shock, graft-versus-host reaction, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, lupus erythematosus disseminatus, hemodynamic shock, ischemic pathological conditions (myocardial infarction, myocardial ischemia, coronary vasospasm, angina pectoris, cardiac insufficiency, heart attack), postischemic reperfusion injuries, malaria, mycobacterial infections, meningitis, leprosy, viral infections (HIV, cytomegalovirus, herpes virus), AIDS-related opportunistic infections, tuberculosis, psoriasis, atopic and contact dermatosis, diabetes, cachexia, cancer and radiation-mediated damage, comprising the administration of a compound of formula (I) or of one of its pharmaceutically acceptable salts or solvates, alone or in combination with other active principles.

According to a subsequent aspect, the invention relates to a medicament comprising, as active principle, at least one compound of formula (I) or one of its pharmaceutically acceptable salts or solvates.

The following examples illustrate the invention.

PREPARATION 1

3-[4-(2-(Methylsulfonyloxy)ethyl)phenyl]pyridine (i) 3-[4-(2-Hydroxyethyl)phenyl]pyridine 1 g (6.8 mmol) of (3-pyridyl)diethylborane, 0.87 ml (10.2 mmol) of 2-(4-bromophenyl)ethanol, 1.53 g (27 mmol) of KOH powder, 1.1 g (3.4 mmol) of tetrabutylammonium bromide and 0.39 g (0.34 mmol) of tetrakis(triphenylphosphine)Pd are mixed in 25 ml of anhydrous THF. The mixture is heated at reflux under a stream of argon for 4 hours. The mixture is poured into water, extraction is carried out with ethyl acetate, the organic phase is dried and the solvent is evaporated. The residue is purified by chromatography on a column of silica gel, elution being carried out with a cyclohexane/ethyl acetate=1/1 mixture, the title product thus being obtained.

(ii)
3-[4-(2-(Methylsulfonyloxy)ethyl)phenyl]pyridine 1 g (4.6 mmol) of the product from the preceding stage is dissolved in 6.9 ml of methylene chloride and the solution is cooled to 0° C. 0.64 ml of triethylamine is added, followed, dropwise, by a solution of 0.36 ml (4.6 mmol) of methanesulfonyl chloride in 0.46 ml of methylene chloride. The mixture is stirred at 0° C. for 30 minutes and subsequently at ambient temperature for 4 hours. The mixture is poured into water, extraction is carried out with ethyl acetate, the organic phase is dried and the solvent is evaporated. The residue is purified by chromatography on a column of silica gel, elution being carried out with a cyclohexane/ethyl acetate=2/8 mixture, the title product thus being obtained.

M.p. 66–68° C.

PREPARATION 2

2-[4-(2-(Methylsulfonyloxy)ethyl)phenyl]pyridine (i) 2-[4-(2-Hydroxyethyl)phenyl]pyridine 1 ml (10.5 mmol) of 2-bromopyridine in 80 ml of anhydrous THF is cooled to −78° C. under a stream of argon, 9.4 ml (15 mmol) of 1.6N n-BuLi in hexane are added thereto and the mixture is stirred for 30 minutes. 3.2 ml (12 mmol) of tributyltin chloride are thus added and the mixture is stirred, still at −78° C., for 2 hours and afterwards at −20° C. for 3 hours. It is poured into an aqueous $NH_4Cl$ solution and extracted with ethyl acetate. The organic phase is dried and the solvent is evaporated. The residue is purified by chromatography on a column of silica gel, elution being carried out with a cyclohexane/ethyl acetate=9/1 mixture, 2.5 g of 2-(tributyltin)pyridine thus being obtained in the form of a yellow oil. 0.31 g of the product thus obtained is dissolved in 5 ml of toluene, and 0.13 ml (0.92 mmol) of 2-(4-bromophenyl)ethanol and 49 mg (0.042 mmol) of tetrakis(triphenylphosphine)Pd are added thereto. The mixture is heated at reflux under a stream of argon for 6 hours. The mixture is poured into water, extraction is carried out with ethyl acetate, the organic phase is dried and the solvent is evaporated. The residue is purified by chromatography on a column of silica gel, elution being carried out with a cyclohexane/ethyl acetate=1/1 and subsequently 4/6 mixture, the title product thus being obtained.

(ii) 2-[4-(2-(Methylsulfonyloxy)ethyl)phenyl]pyridine

By carrying out the reaction as described in Preparation 1(ii) but using the product from the preceding stage instead of the product from Preparation 1(i), the title compound is obtained.

PREPARATION 3

(4-(4-Pyridyl)phenyl)acetic acid (i) 4-(4-Pyridyl)acetophenone 0.85 g (5.6 mmol) of 4-bromopyridine, 1 g (6.1 mmol) of (4-acetylphenyl)boronic acid, 1.26 g (12 mmol) of sodium carbonate and 260 mg of tetrakis(triphenylphosphine)Pd are mixed in 25 ml of THF and 6 ml of water. The mixture is heated at 90° C. under a stream of nitrogen for 2 hours. The mixture is poured into water, extraction is carried out with diethyl ether, the organic phase is dried and the solvent is evaporated. The residue is purified by chromatography on a column of silica gel, elution being carried out with a cyclohexane/ethyl acetate=3/7 mixture, the title product thus being obtained in the form of a white solid.

M.p. 88–90° C.

(ii) (4-(4-Pyridyl)phenyl)acetic acid 1.5 g (7.6 mmol) of the product from the preceding stage, 0.29 g of sulfur, 3.6 ml of morpholine and a catalytic amount of p-toluenesulfonic acid monohydrate are mixed and the mixture is heated at 130° C. under a stream of nitrogen. After 6 hours, the mixture is cooled, 7 ml of absolute ethanol are added and the mixture is stirred at ambient temperature overnight. 1.5 g of thioamide thus formed are dissolved in a solution of 12.3 ml of ethanol, 56.2 ml of water and 0.6 g of NaOH, and the solution is heated at reflux for 3 hours. It is subsequently acidified with a dilute hydrochloric acid solution and the solvents are evaporated. The title compound is thus obtained.

PREPARATION 4

(4-(6-Methylpyrid-3-yl)phenyl)acetic acid (i) 4-(6-Methylpyrid-3-yl)acetophenone 0.25 g (1.1 mol) of 3-trifluoromethylsulfonate-6-methylpyridine, 0.18 g (1 mmol) of (4-acetylphenyl)boronic acid, 1.3 ml of a 2M sodium carbonate solution, 38 mg of tetrakis(triphenylphosphine)Pd and 85 mg (2 mmol) of LiCl are mixed in 9 ml of anhydrous 1,2-dimethoxyethane. The mixture is heated at 75° C. for 3 hours. The mixture is poured into water, extraction is carried out with diethyl ether, the organic phase is dried and the solvent is evaporated. The residue is treated in hexane and the title product is thus obtained in the form of a white solid.

M.p. 94–96° C.

(ii) (4-(6-Methylpyrid-3-yl)phenyl)acetic acid

By carrying out the reaction as described in Preparation 3(ii) but using the product from the preceding stage instead of the product from Preparation 3(i), the title compound is obtained.

PREPARATION 5

3-[3-(2-Bromoethyl)phenyl]pyridine Hydrobromide (i) 3-[3-(2-Hydroxyethyl)phenyl]pyridine By carrying out the reaction as described in Preparation 1 but using 2-(3-bromophenyl)ethanol instead of 2-(4-bromophenyl)ethanol, the title compound is obtained.

(ii) 3-[3-(2-Bromoethyl)phenyl]pyridine Hydrobromide

The product from the preceding stage is dissolved in 6 ml of 48% hydrobromic acid and the solution is heated at 125° C. for 6 hours. Dilution is carried out with 2 ml of water and the precipitated product is filtered off. The title product is thus obtained.

PREPARATION 6

(4-(5-Pyrimidinyl)phenyl)acetic acid (i) 4-(5-Pyrimidinyl)acetophenone

By carrying out the reaction as described in Preparation 4 but using 5-bromopyrimidine instead of 3-trifluoromethanesulfonate-6-methylpyridine, the title compound is obtained. M.p. 134–136° C.

(ii) (4-(5-Pyrimidinyl)phenyl)acetic acid

By carrying out the reaction as described in Preparation 3(ii) but using the product from the preceding stage instead of the product from Preparation 3(i), the title compound is obtained.

PREPARATION 7

4-[3-(2-Bromoethyl)phenyl]pyridine

By carrying out the reaction as described in Preparation 5 but using 4-(4,4,5,5-tetramethyl[1,3,2]dioxaboran-2-yl)pyridine instead of (3-pyridyl)diethylborane, the title compound is obtained in the form of a yellow oil.

PREPARATION 8

2-[3-(2-Chloroethyl)phenyl]pyridine (i) 2-[3-(2-Hydroxyethyl)phenyl]pyridine

By carrying out the reaction as described in Preparation 2(i) but using 2-(3-bromophenyl)ethanol instead of 2-(4-bromophenyl)ethanol, the title compound is obtained in the form of a yellow oil.

(ii) 2-[3-(2-Chloroethyl)phenyl]pyridine

The product from the preceding stage in 17 ml of dichloromethane is cooled to 0° C. and 11 ml of $SOCl_2$ are added thereto. The mixture is stirred overnight at ambient temperature and is poured into a water/ice mixture, the pH is brought to neutrality by addition of sodium bicarbonate, extraction is carried out with dichloromethane, the organic phase is dried and the solvent is evaporated. The title compound is obtained in the form of a yellow oil.

PREPARATION 9

4-[3-(2-Chloroethyl)phenyl]pyridine (i) 4-[3-(2-Hydroxyethyl)phenyl]pyridine

By carrying out the reaction as described in Preparation 5(i) but using 4-(4,4,5,5-tetramethyl [1,3,2]dioxaboran-2-yl)pyridine instead of (3-pyridyl)diethylborane, the title compound is obtained in the form of a yellow oil.

(ii) 4-[3-(2-Chloroethyl)phenyl]pyridine

By carrying out the reaction as described in Preparation 8(ii) but using the product from the preceding stage, the title compound is obtained in the form of a yellow oil.

PREPARATION 10

3-[3-(2-Chloroethyl)-4-methylphenyl]pyridine (i) 4-[3-(2-Hydroxyethyl)-4-methylphenyl]pyridine By carrying out the reaction as described in Preparation 1(i) but using 2-(3-bromo-4-methylphenyl)ethanol instead of 2-(4-bromophenyl)ethanol, the title compound is obtained.

(ii) 4-[3-(2-Chloroethyl)-4-methylphenyl]pyridine

By carrying out the reaction as described in Preparation 8(ii) but using the product from the preceding stage, the title compound is obtained.

PREPARATION 11

3-(4-Pyridyl 1-oxide)phenylacetaldehyde 2.5 g (0.015 mol) of 4-(3-hydroxyphenyl)pyridine and 40 ml of pyridine and 2.3 g of 4-(dimethylamino)pyridine (DMAP) are cooled to 0° C. 3.2 ml of triflic anhydride are added thereto dropwise. The mixture is stirred at 0° C. for one hour and at ambient temperature overnight. It is poured into a water/ice mixture, extraction is carried out with ethyl acetate, the organic phase is dried and the solvent is evaporated under reduced pressure. The crude product is purified by chromatography on a column of silica gel, elution being carried out with a cyclohexane/ethyl acetate=8/2 mixture. 4-(3-Hydroxyphenyl)pyridine trifluoromethanesulfonate is obtained in the form of an oil. 2.26 g of this product are mixed with 112 ml of anhydrous dimethylformamide, 38 g of palladium acetate, 2.5 ml of anhydrous triethylamine and 2 g of N,N-dimethylethanolamine vinyl ether. The mixture is heated at 80° C. for 48 hours. The solvent is evaporated under reduced pressure. The residue is purified by flash chromatography on a column of silica gel, elution being carried out with ethyl acetate, to remove the first product, and subsequently with an ethyl acetate/methanol=1/1 mixture. 2-[2-[3-(4-Pyridyl)-phenyl)ethenyl)oxy)]-N,N-dimethyl-1-ethanamine is obtained. 0.53 g of this product, dissolved in 35 ml of methanol, is treated with 20 ml of water and 5 ml of 96% sulfuric acid. The mixture is heated at 60° C. for 6 hours and is poured into ice, a saturated aqueous $NaHCO_3$ solution is added thereto and extraction is carried out with ethyl acetate. The organic phase is dried and the solvent is evaporated under reduced pressure. 3-(4-Pyridyl)phenylacetaldehyde dimethyl acetal is obtained. Its N-oxide derivative is prepared by reaction with m-chloroperbenzoic acid in methylene chloride and the aldehyde is subsequently released by reaction with a mixture of trifluoroacetic acid, water and methylene chloride. The title compound is thus obtained.

EXAMPLE 1

1-[2-(4-(3-Pyridyl)phenyl)ethyl]-4-(3-(trifluoromethyl)phenyl)-1,2,3,6-tetrahydropyridine and its dihydrochloride 0.85 g (2.9 mmol) of the product from Preparation 1 is dissolved in 14 ml of isopropanol, and 1.21 ml of triethylamine and 700 mg (2.9 mmol) of 4-(3-(trifluoromethyl)phenyl)-1,2,3,6-tetrahydropyridine are added thereto. The mixture is heated at reflux for 4 hours, is poured into water and is extracted with ethyl acetate. The organic phase is dried, the solvent is evaporated under reduced pressure and the crude prdouct is obtained, which product is purified by chromatography on a column of silica gel, elution being carried out with ethyl acetate. The title product is thus obtained. Its dihydrochloride salt is prepared by reaction with of the acid of a solution of isopropanol saturated with hydrochloric acid.

M.p. 235–257° C. (dihydrochloride)

EXAMPLE 2

1-[2-(4-(2-Pyridyl)phenyl)ethyl]-4-(3-(trifluoromethyl)phenyl)-1,2,3,6-tetrahydropyridine and its dihydrochloride By carrying out the reaction as described in Example 1 but using the product from Preparation 2, the title compound is obtained. The hydrochloride is prepared using a solution of isopropanol saturated with hydrochloric acid.

M.p. 253–256° C. (hydrochloride)

EXAMPLE 3

1-[2-(4-(4-Pyridyl)phenyl)ethyl]-4-(3-(trifluoromethyl)phenyl)-1,2,3,6-tetrahydropyridine and its dihydrochloride 2.4 g of the product from Preparation 3 are dissolved in 20 ml of methylene chloride, 1.23 g (5 mmol) of 4-hydroxy-4-(3-(trifluoromethyl)phenyl)piperidine, 2.2 g (5 mmol) of BOP and 2.1 ml of triethylamine are added thereto and the mixture is stirred at ambient temperature overnight. A mixture of ethyl acetate and of water is added, the two phases are separated, the organic phase is dried over sodium sulfate and the solvent is evaporated. The crude product is purified by chromatography on a column of silica gel, elution being carried out with an ethyl acetate/methanol=9/1 mixture. 1.1 g of the product thus obtained, dissolved in 32 ml of anhydrous THF, are poured into a suspension of 0.19 g (5 mmol) of $LiAlH_4$ in 4.5 ml of anhydrous THF at 0° C. under a stream of nitrogen. The mixture is stirred at ambient temperature for 5 hours, is poured into a water/ice mixture and is extracted with ethyl acetate. The two phases are separated, the organic phase is dried over sodium sulfate and the solvent is evaporated. 0.65 g of the product, thus reduced, is dissolved in 3.9 ml of acetic acid, 0.78 ml of 96% sulfuric acid is added thereto and the mixture is heated at 80° C. for 2 hours. It is poured into an NaOH/ice mixture and is extracted with ethyl acetate. The organic phase is washed with water, is dried and is evaporated under reduced pressure. The crude product is purified by chromatography on a column of silica gel, elution being carried out with an ethyl acetate/methanol=95/5 mixture. The title compound is thus obtained. The dihydrochloride salt is prepared using a solution of isopropanol saturated with hydrochloric acid.

M.p. 179–181° C. (dihydrochloride)

EXAMPLE 4

1-[2-(4-(6-Methylpyrid-3-yl)phenyl)ethyl]-4-(3-(trifluoromethyl)phenyl)-1,2,3,6-tetrahydropyridine and its dihydrochloride By carrying out the reaction as described in Example 3 but using the product from Preparation 4, the title compound is obtained.

M.p. 174–175° C. (dihydrochloride)

EXAMPLE 5

1-[2-(3-(3-Pyridyl)phenyl)ethyl]-4-(3-(trifluoromethyl)phenyl)-1,2,3,6-tetrahydropyridine and its dioxalate By carrying out the reaction as described in Example 1 but using the product from Preparation 5 (free base), butanol instead of propan-2-ol and potassium carbonate instead of triethylamine, the title compound is obtained. Its oxalate salt is prepared by treatment of the base with oxalic acid in acetone.

M.p. 152–157° C. (dioxalate)

EXAMPLE 6

1-[2-(4-(5-Pyrimidinyl)phenyl)ethyl]-4-(3-(trifluoromethyl)phenyl)-1,2,3,6-tetrahydropyridine and its hydrochloride By carrying out the reaction as described in Example 3 but using the product from Preparation 6, the title compound is obtained.

M.p. 196–198° C. (hydrochloride)

EXAMPLE 7

1-[2-(3-(4-Pyridyl)phenyl)ethyl]-4-(3-(trifluoromethyl)phenyl)-1,2,3,6-tetrahydropyridine and its dioxalate Salt By carrying out the reaction as described in Example 1 but using the product from Preparation 7, the title compound is obtained in the form of an oil. Its oxalate salt is prepared by treatment of the base with oxalic acid in acetone.

M.p. 140–144° C. (dioxalate)

EXAMPLES 8 TO 16

By following the reaction scheme of Example 1 but using appropriate starting materials, the compounds listed in the table below are obtained:

Ex. 8[(1)] 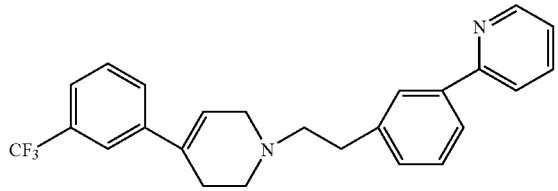 Oxalate salt
M.p. 182–186° C.
Ex. 9[(1)] 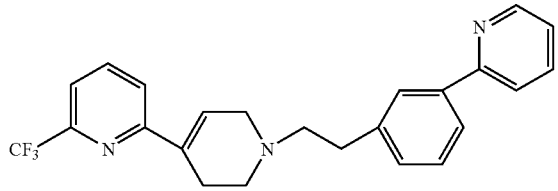 Oxalate salt
M.p. 126–129° C.
Ex. 10[(1)] 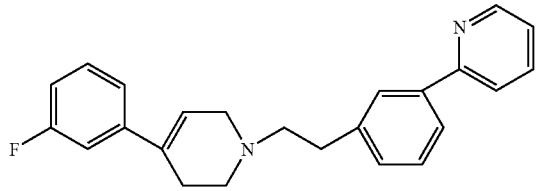 Oxalate salt
M.p. 175–177° C.
Ex. 11[(2)] 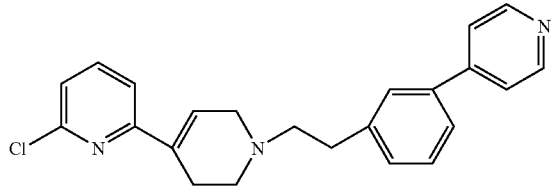 Oxalate salt
M.p. 183–186° C.
Ex. 12[(3)] 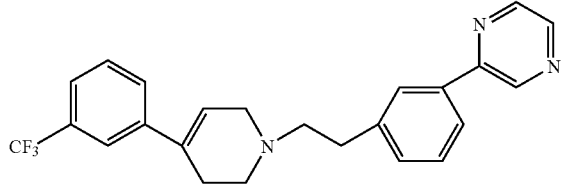 Oxalate salt
M.p. 205–207° C.
Ex. 13[(3)] 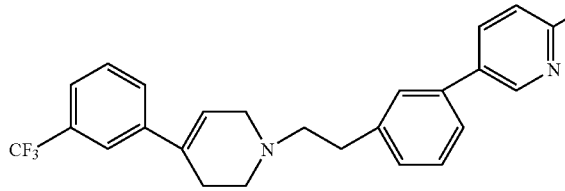 Oxalate salt
M.p. 170–173° C.
Ex. 14[(3)] 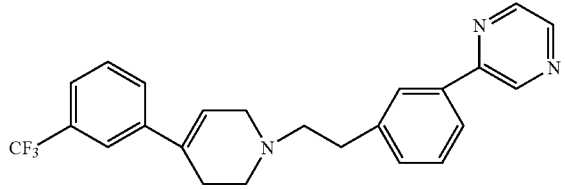 Oxalate salt
M.p. 199–201° C.
Ex. 15[(3)] 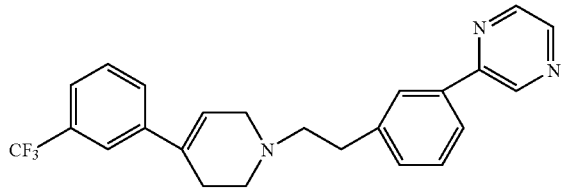 Mass: M+ 409
TLC: R.f. 0.35
(AcEt/MeOH = 8/2)

| Ex. 16[(4)] | 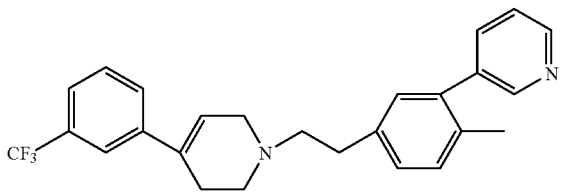 | TLC: R.f. 0.6 (AcEt) |
|---|---|---|

Notes:

The starting materials are described in the above Preparations or else they can be prepared analogously to the latter; in particular:

(1) intermediate described in Preparation 8
(2) intermediate described in Preparation 9
(3) intermediates obtained by reaction of [3-(2-hydroxyethyl)phenyl]boronic acid with appropriate haloheterocycles
(4) intermediate described in Preparation 10

The reaction solvent is preferably 4-methyl-2-pentanone (instead of the isopropanol described in Example 1)

TLC=thin layer chromatography
AcEt=ethyl acetate
MeOH=methanol

EXAMPLE 17

1-[2-(3-(4-Pyridyl)phenyl)ethyl]-4-(3-(trifluoromethyl)phenyl)-1,2,3,6-tetrahydropyridine 1-oxide The N-oxide derivative of the compound of Example 7 is prepared by reaction with m-chloroperbenzoic acid in methylene chloride.

Thin layer chromatography (TLC): R.f. 0.15, eluent methanol.

EXAMPLE 18

1-[2-(3-(4-Pyridyl 1-oxide)phenyl)ethyl]-4-(3-(trifluoromethyl)phenyl)-1,2,3,6-tetrahydropyridine 0.24 g (0.001 mol) of 4-(3-(trifluoromethyl)phenyl)-1,2,3,6-tetrahydropyridine, 12 ml of methanol, 0.26 ml of glacial acetic acid and 0.12 g of sodium acetate are mixed. The mixture is cooled to 0–5° C. and 8 ml of methanol, 0.37 g of 3-(4-pyridyl 1-oxide)phenylacetaldehyde (as obtained by Preparation 11) and, with care, 0.2 g of sodium cyanoborohydride are added thereto. The mixture is stirred at 0–5° C. for 0.5 hour and subsequently at ambient temperature overnight. 3 ml of concentrated hydrochloric acid are added, the mixture is stirred for 15 minutes, the solvent is evaporated under reduced pressure and the residue is taken up in an ethyl acetate/NH$_4$OH mixture. The organic phase is dried over sodium sulfate and filtered, and the solvent is evaporated. The residue is purified by chromatography on a column of silica gel, elution being carried out with an ethyl acetate/methanol=8/2 mixture. The title compound is obtained.

M.p. 142–145° C.

What is claimed is:

1. A compound of formula (1):

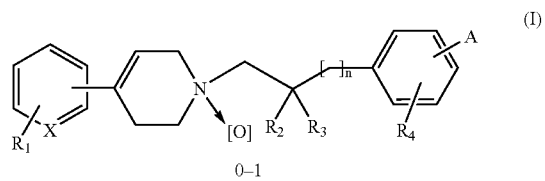

(I)

in which
X is N or CH;
R$_1$ is a hydrogen or halogen atom or a CF$_3$ group;
R$_2$ and R$_3$ independently are a hydrogen atom or a (C$_1$–C$_4$)alkyl group;
R$_4$ is a hydrogen atom or a (C$_1$–C$_4$)alkyl group;
n is 0 or 1; and
A is a nitrogenous hetereocycle of formula (a)–(d):

(a)

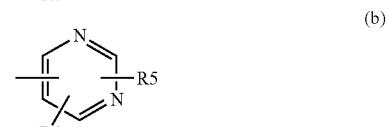

(b)

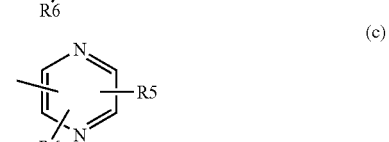

(c)

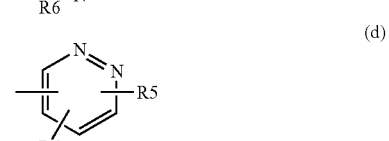

(d)

where R$_5$ and R$_6$ each independtly are a hydrogen atom or a (C$_1$–C$_4$)alkyl or (C$_1$–C$_4$)alkoxy group;
or an N-oxide, salt or solvate ihereof.

2. The compound as claimed in claim 1, where n is zero.
3. The compound as claimed in claim 1, where R$_2$ and R$_3$ are each hydrogen.
4. The compound as claimed in claim 1, where R$_1$ is a CF$_3$ group.
5. The compound as claimed in claim 1, where X is CH and R$_1$ is in the 3-position of the benzene.

6. The compound as claimed in claim 1, where X is N and the pyridine thus formed is substituted in the 2,6-positions.

7. The compound as claimed in claim 1, where the phenyl ring is substituted by the notrogenous heterocycle A in the 3-position.

8. The compound as claimed in claim 1 in the form of an N-oxide thereof.

9. A compound selected from the group consisting of:
1-[2-(4-(3-Pyridyl)phenyl)ethyl]-4-(3-(trifluoromethyl)phenyl)-1,2,3,6-tetrahydropyridine;
1-[2-(4-(2-Pyridyl)phenyl)ethyl]-4-(3-(trifluoromethyl)phenyl)-1,2,3,6-tetrahydropyridine;
1-[2-(4-(4-Pyridyl)phenyl)ethyl]-4-(3-(trifluoromethyl)phenyl)-1,2,3,6-tetrahydropyridine;
1-[2-(4-(6-Methylpyrid-3-yl)phenyl)ethyl]-4-(3-(triflouronmethyl)phenyl)-1,2,3,6-tetrahydropyridine;
1-[2-(3-(3-Pyridyl)phenyl)ethyl]-4-(3-(trifluoromethyl)phenyl)-1,2,3,6-tetrahydropyridine;
1-[2-(4-(5-Pyrimidinyl)phenyl)ethyl]-4-(3-(trifluoromethyl)phenyl)-1,2,3,6-tetrahydropyridine;
1-[2-(3-(4-Pyridyl)phenyl)ethyl]-4-(3-(trifluoromethyl)phenyl)-1,2,3,6-tetrahydropyridine;
1-[2-(3-(2-Pyridyl)phenyl)ethyl]-4-(3-(trifluoromethyl)phenyl)-1,2,3,6-tetrahydropyridine;
1-[2-(3-(2-Pyridyl)phenyl)ethyl]-4-(6-(trifluoromethyl)pyrid-2-yl)-1,2,3,6-tetrahydropyridine;
1-[2-(3-(2-Pyridyl)phenyl)ethyl]-4-(3-flourophenyl)-1,2,3,6-tetrahydropyridine;
1-[2-(3-(4-Pyridyl)phenyl)ethyl]-4-(6-chloropyrid-2-yl)-1,2,3,6-tetrahydropyridine;
1-[2-(3-(2-Pyrazinyl)phenyl)ethyl]-4-(3-(trifluoromethyl)phenyl)-1,2,3,6-tetrahydropyridine;
1-[2-(3-(6-Methyl-3-pyridyl)phenyl)ethyl]-4-(3-(trifluoromethyl)phenyl)-1,2,3,6-tetrahydropyridine;
1-[2-(3-(2-Pyrimidiyl)phenyl)ethyl]-4-(3-(trifluoromethyl)phenyl)-1,2,3,6-tetrahydropyridine;
1-[2-(3-(3-Pyridaziyl)phenyl)ethyl]-4-(3-(trifluoromethyl)phenyl)-1,2,3,6-tetrahydropyridine;
1-[2-(3-(3-Pyridyl)-4-methylphenyl)ethyl]-4-(3-(trifluoromethyl)phenyl)-1,2,3,6-tetrahydropyridine;
1-[2-(3-(4-Pyridyl)phenyl)ethyl]-4-(3-(trifluoromethyl)phenyl)-1,2,3,6-tetrahydropyridine 1-oxide; and
1-[2-(3-(4-Pyridyl 1-oxide)phenyl)ethyl]-4-(3-(trifluoromethyl)phenyl)-1,2,3,6-tetrahydropyridine; or salt or solvent thereof.

10. A process for the preparation of the compound of formula (I) comprising reacting a compound of formula (II)

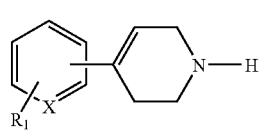

in which X and $R_1$ are as defined in claim 1, with a compound of formala (III):

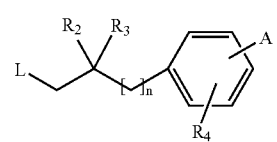

in which $R_2$, $R_3$, $R_4$, n and A are as defined in claim 1 and L is a leaving group, isolating the compound of formula (I), and optionally converting the compound of formula (I) to a salt, solvate or N-oxide thereof.

11. A pharmaceutical composition, comprising the comnound of formula (I) as claimed in claim 1 or a solvate or pharmaceutically acceptable salt thereof and a pharmaceutically acceptable carrier.

12. The composition as claimed in claim 11 comprising 0.001 to 100 mg of the compound of formula (I).

13. A method for the treatment of pain comprising administering to a patient in need of such treatment an effective amount of the compound according to claim 1 or salt or solvate thereof.

14. The compound as claimed in claim 2 in the form of an N-oxide thereof.

15. The compound as claimed in claim 3 in the form of an N-oxide thereof.

16. The compound as claimed in claim 4 in the form of an N-oxide thereof.

17. The compound as claimed in claim 5 in the form of an N-oxide thereof.

18. The compound as claimed in claim 6 in the form of an N-oxide thereof.

19. The compound as claimed in claim 7 in the form of an N-oxide thereof.

20. A pharmaceutical composition, comprising the compound of formula (I) as claimed in claim 2 or solvate or pharmaceutically acceptable salt thereof and a pharmaceutically acceptable carrier.

21. A pharmaceutical composition, comprising the compound or formula (I) as claimed in claim 3 or solvate or pharmaceutically acceptable salt thereof and a pharmaceutically acceptable carrier.

22. A pharmaceutical composition, comprising the compound of formula (I) as claimed in claim 4 or solvate or pharmaceutically acceptable salt thereof and a pharmaceutically acceptable carrier.

23. A pharmaceutical composition, comprising the compound of formula (I) as claimed in claim 5 or solvate or pharmaceutically acceptable salt thereof and a pharmaceutically acceptable carrier.

24. A pharmaceutical composition, comprising the compound of formula (I) as claimed in claim 6 or solvate or pharmaceutically acceptable salt thereof and a pharmaceutically acceptable carrier.

25. A pharmaceutical composition, comprising the compound of formula (I) as claimed in claim 7 or solvate or pharmaceutically acceptable salt thereof and a pharmaceutically acceptable carrier.

26. A pharmaceutical composititon, comprising the compound of formula (I) as claimed in claim 8 or solvate or pharmaceutically acceptable salt thereof and a pharmaceutically acceptable carrier.

27. A pharmaceutical composition, comprising the compound of formula (I) as claimed in claim 9 or solvate or pharmaceutically acceptable salt thereof and a pharmaceutically acceptable carrier.

28. A pharmaceutical composition, comprising the compound of formula (I) as claimed in claim 14 or solvate or pharmaceutically acceptable salt thereof and a pharmaceutically acceptable carrier.

29. A pharmaceutical composition, comprising the compound of formula (I) as claimed in claim 15 or solvate or pharmaceutically acceptable salt thereof and a pharmaceutically acceptable carrier.

30. A pharmaceutical composition, comprising the compound of formula (I) as claimed in claim 16 or solvate or pharmaceutically acceptable salt thereof and a pharmaceutically acceptable carrier.

31. A pharmaceutical composition, comprising the compound of formula (I) as claimed in claim 17 or solvate or pharmaceutically acceptable salt thereof and a pharmaceutically acceptable carrier.

32. A pharmaceutical composition, comprising the compound of formula (I) as claimed in claim 18 or solvate or pharmaceutically acceptable salt thereof and a pharmaceutically acceptable carrier.

33. A pharmaceutical composition, comprising the compound of formula (I) as claimed in claim 19 or solvate or pharmaceutically acceptable salt thereof and a pharmaceutically acceptable carrier.

34. A method for the treatment of pain comprising administering to a patient in need of such treatment an effective amount of the compound according to claim 2 or salt or solvate thereof.

35. A method for the treatment of pain comprising administering to a patient in need of such treatment an effective amount of the compound according to claim 3 or salt or solvate thereof.

36. A method for the treatment of pain comprising administering to a patient in need of such treatment an effective amount of the compound according to claim 4 or salt or solvate thereof.

37. A method for the treatment of pain comprising administering to a patient in need of such treatment an effective amount of the compound according to claim 5 or salt or solvate thereof.

38. A method for the treatment of pain comprising administering to a patient in need of such treatment an effective amount of the compound according to claim 6 or salt or solvate thereof.

39. A method for the treatment of pain comprising administering to a patient in need of such treatment an effective amount of the compound according to claim 7 or salt or solvate thereof.

40. A method for the treatment of pain comprising administering to a patient in need of such treatment an effective amount of the compound according to claim 8 or salt or solvate thereof.

41. A method for the treatment of pain comprising administering to a patient in need of such treatment an effective amount of the compound according to claim 9 or salt or solvate thereof.

42. A method for the treatment of pain comprising administering to a patient in need of such treatment an effective amount of the compound according to claim 14 or salt or solvate thereof.

43. A method for the treatment of pain comprising administering to a patient in need of such treatment an effective amount of the compound according to claim 15 or salt or solvate thereof.

44. A method for the treatment of pain comprising administering to a patient in need of such treatment an effective amount of the compound according to claim 16 or salt or solvate thereof.

45. A method for the treatment of pain comprising administering to a patient in need of such treatment an effective amount of the compound according to claim 17 or salt or solvate thereof.

46. A method for the treatment of pain comprising administering to a patient in need of such treatment an effective amount of the compound according to claim 18 or salt or solvate thereof.

47. A method for the treatment of pain comprising administering to a patient in need of such treatment an effective amount of the compound according to claim 19 or salt or solvate thereof.

* * * * *